United States Patent
Lee et al.

(10) Patent No.: US 11,540,823 B2
(45) Date of Patent: Jan. 3, 2023

(54) SOFT TISSUE FIXING ANCHOR AND SOFT TISSUE FIXING METHOD USING THE SAME

(71) Applicants: Ho Jong Lee, Yongin-si (KR); Sung Wook Hwang, Seongnam-si (KR)

(72) Inventors: Ho Jong Lee, Yongin-si (KR); Sung Wook Hwang, Seongnam-si (KR)

( * ) Notice: Subject to any disclaimer, the term of this patent is extended or adjusted under 35 U.S.C. 154(b) by 391 days.

(21) Appl. No.: 16/861,232

(22) Filed: Apr. 29, 2020

(65) Prior Publication Data

US 2021/0338222 A1 Nov. 4, 2021

(51) Int. Cl.
*A61B 17/04* (2006.01)

(52) U.S. Cl.
CPC .. *A61B 17/0401* (2013.01); *A61B 2017/0403* (2013.01); *A61B 2017/0464* (2013.01)

(58) Field of Classification Search
CPC .... A61B 17/0642; A61B 17/0401–2017/0464; A61F 2/0811–2002/0888
See application file for complete search history.

(56) References Cited

U.S. PATENT DOCUMENTS

| | | | |
|---|---|---|---|
| 5,084,050 A * | 1/1992 | Draenert | A61F 2/30767 606/313 |
| 5,354,298 A * | 10/1994 | Lee | A61B 17/0401 606/139 |
| 5,464,425 A * | 11/1995 | Skiba | A61B 17/0401 606/232 |
| 5,507,812 A * | 4/1996 | Moore | A61F 2/08 623/13.13 |
| 5,569,306 A * | 10/1996 | Thal | A61F 2/0811 606/232 |
| 5,584,835 A * | 12/1996 | Greenfield | A61B 17/0401 606/232 |
| 5,718,717 A * | 2/1998 | Bonutti | A61B 17/0401 606/232 |
| 7,070,622 B1 * | 7/2006 | Brown | A61F 2/38 623/20.14 |
| 2008/0033487 A1 * | 2/2008 | Schwartz | A61B 17/0469 606/232 |
| 2008/0097604 A1 * | 4/2008 | Strobel | A61F 2/0811 623/13.14 |
| 2008/0109080 A1 * | 5/2008 | Aeschlimann | A61C 8/0016 623/16.11 |
| 2009/0287309 A1 * | 11/2009 | Walch | A61L 27/16 623/18.11 |
| 2010/0036416 A1 * | 2/2010 | Martin | A61B 17/0401 606/232 |
| 2010/0256677 A1 * | 10/2010 | Albertorio | A61F 2/0811 606/232 |
| 2011/0118744 A1 * | 5/2011 | Lehmann | A61B 17/686 606/104 |

(Continued)

*Primary Examiner* — Tan-Uyen T Ho
*Assistant Examiner* — Charles M Wei
(74) *Attorney, Agent, or Firm* — Revolution IP, PLLC

(57) ABSTRACT

A soft tissue fixing anchor includes: an anchor member which is inserted to the bone cavity interior and prevented from moving in the bone cavity interior by the artificial joint when the artificial joint is implanted; and a suture of which one end portion is fixed to the anchor member and the other end portion is exposed to a bone cavity exterior of the bone so as to be sutured to the soft tissue.

2 Claims, 4 Drawing Sheets

(56) References Cited

U.S. PATENT DOCUMENTS

2011/0319994 A1* 12/2011 Tepic .................... A61F 2/0811
 623/13.14
2014/0005721 A1* 1/2014 Mayer ................ A61B 17/0401
 606/232

* cited by examiner

[FIG 1]
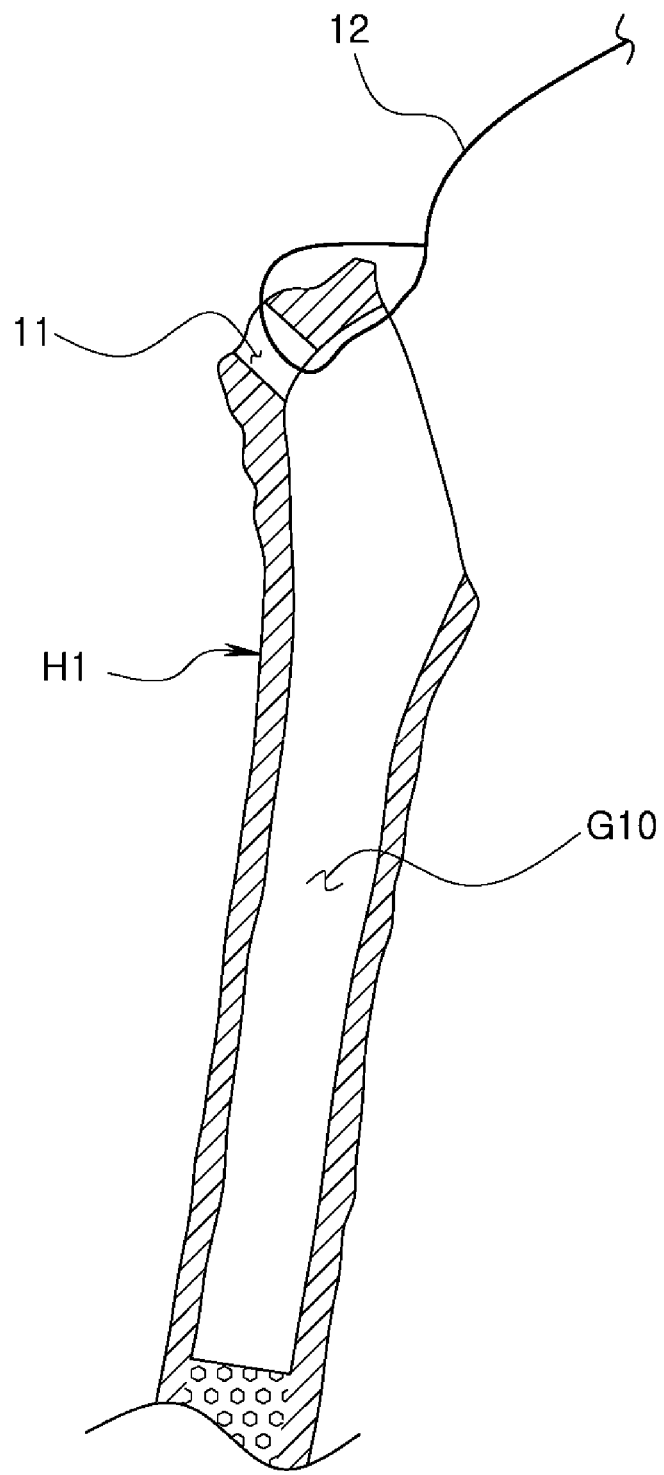

[FIG 2]
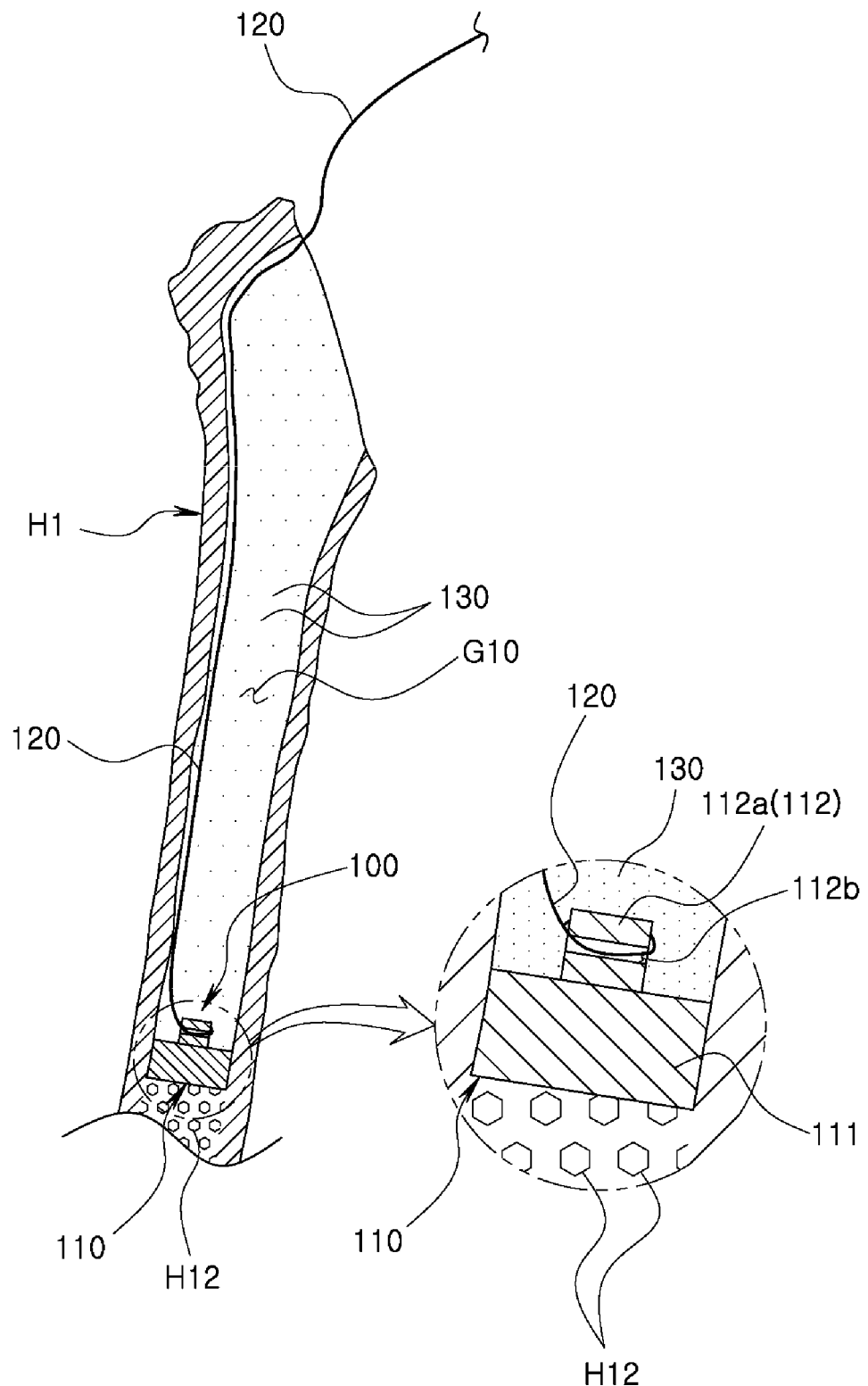

[FIG. 3]
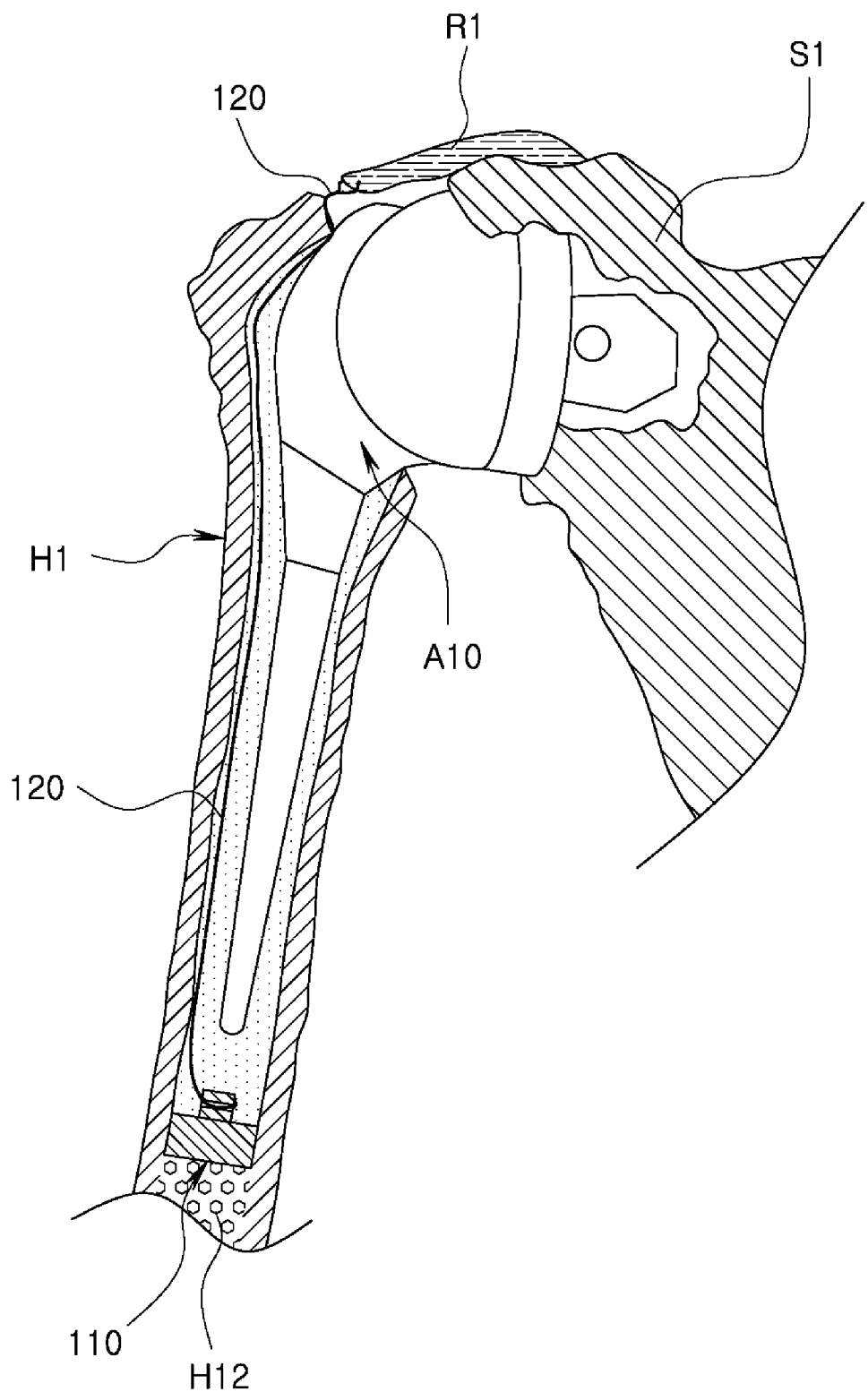

[FIG. 4]
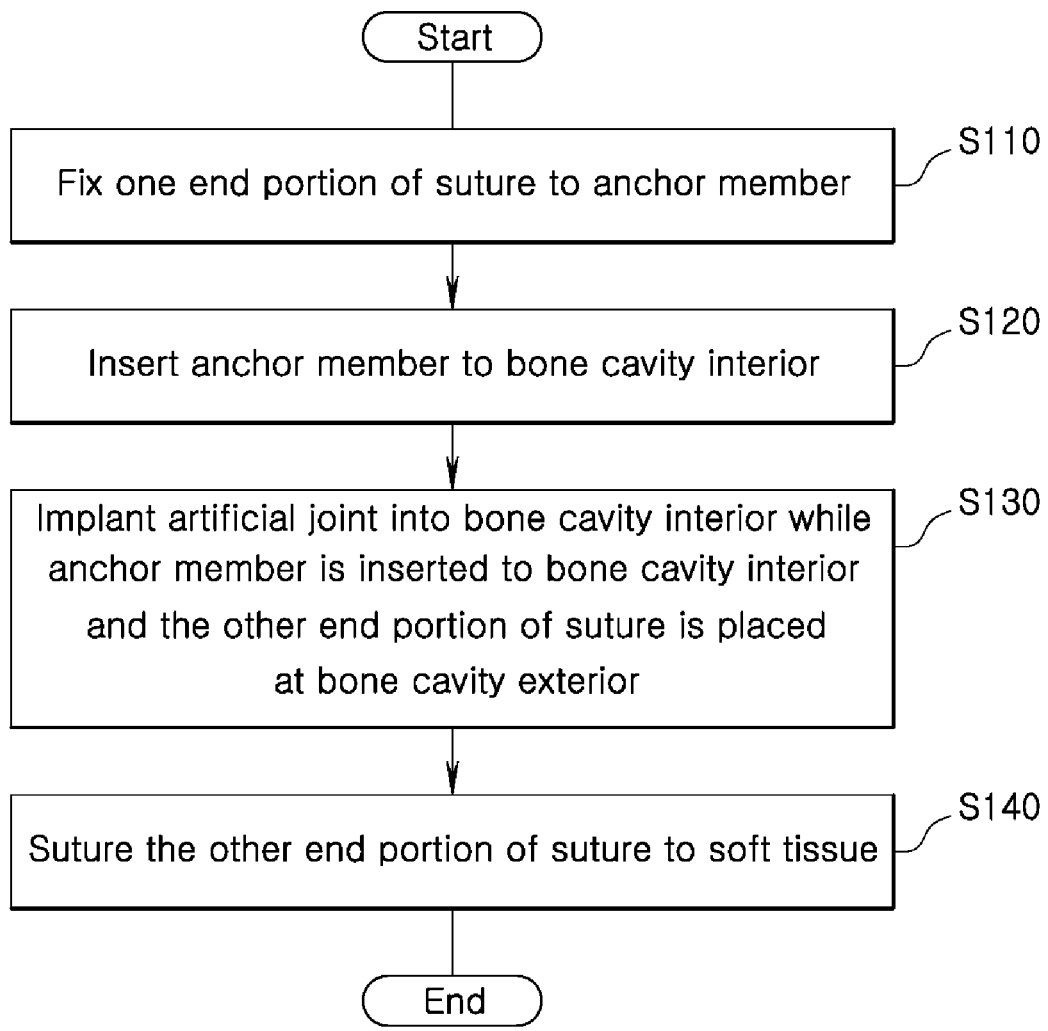

SOFT TISSUE FIXING ANCHOR AND SOFT TISSUE FIXING METHOD USING THE SAME

TECHNICAL FIELD

The present invention relates to a soft tissue fixing anchor for fixing a soft tissue.

BACKGROUND ART

In general, a soft tissue is a tissue comprising the human body and refers to a tissue such as a ligament, a tendon, and a joint sac. These soft tissues may be divided into tissues that are attached to bones and tissues that are not attached to the bones.

Here, in the case of the tissue attached to the bone, there is a tissue such as a rotator cuff connecting the scapula and the humerus, a tissue such as a ligament connecting the pelvis and the femur, or a tissue such as a ligament connecting the humerus and the forearm.

The tissue attached to the bone may be deformed or ruptured due to aging or trauma, or an end thereof may be peeled from the bone (full-thickness tear). In this case, treatments for fixing the soft tissue are performed.

These treatments may be divided into a non-surgical treatment and a surgical treatment according to a degree of damage. The non-surgical treatment is a conservative treatment performed through drugs or exercise, and the surgical treatment is a treatment in which a damaged tissue is pulled with a suture and fixed to the bone.

Meanwhile, if avascular necrosis occurs at an end portion of the bone, the end portion of the bone is replaced with an artificial joint. To replace the artificial joint, as illustrated in FIG. 1, first, the soft tissue (not illustrated) is peeled from the bone, and then an end portion (not illustrated) of the necrotic bone is cut, a bone cavity tissue of the remaining bone H1 is removed, a hole 11 is drilled in the bone H1 from which the bone cavity tissue is removed by using a drill and the like, and a suture 12 is connected to the hole 11. Thereafter, an artificial joint (not illustrated) is implanted into a bone cavity interior G10, and the suture 12 is connected to the peeled soft tissue (not illustrated) to fix the soft tissue.

However, since an existing soft tissue fixing technology has a technical configuration of drilling the hole 11 for connecting the suture 12 to the bone H1, there is a problem that bone loss occurs, and since a significant tensile force is applied to the suture 12 connecting the hole 11 of the bone H1 and the soft tissue (not illustrated), in the case of a patient whose bone is weakened due to aging, there is a problem that the hole portion of the bone does not sustain the tensile force of the suture.

DISCLOSURE

Technical Problem

A technical object of the present invention is to provide a soft tissue fixing anchor and a soft tissue fixing method using the same capable of firmly fixing a soft tissue to a bone without bone loss.

Technical Solution

In order to achieve the object, according to an embodiment of the present invention, a soft tissue fixing anchor, as a soft tissue fixing anchor which is used in a procedure of implanting an artificial joint into a bone cavity interior of a bone by cutting an end portion of the bone and removing a bone cavity tissue of the remaining bone, includes: an anchor member which is inserted to the bone cavity interior and prevented from moving to the bone cavity interior by the artificial joint when the artificial joint is implanted; and a suture of which one end portion is fixed to the anchor member and the other end portion is exposed to a bone cavity exterior of the bone so as to be sutured to the soft tissue.

The anchor member may include a plate-shaped body part; and a fixing part provided in the body part to fix one end portion of the suture.

The body part may be made of a resin material.

The fixing part may include a fixing protrusion protruding from an upper end of the body part; and a through hole formed in the fixing protrusion to penetrate the suture.

One end portion of the suture may be fixed to the anchor member before the anchor member is inserted to the bone cavity interior, and the other end portion of the suture may be exposed to the bone cavity exterior of the bone while the anchor member is inserted to the bone cavity interior.

The suture may be first fixed by the anchor member and second fixed between a bone cavity inner wall of the bone and the artificial joint when the artificial joint is inserted to the bone cavity interior.

In a procedure in which the bone cement is injected to the bone cavity interior before the artificial joint is inserted to the bone cavity interior, the suture may be third fixed by the bone cement.

Meanwhile, according to another embodiment of the present invention, a soft tissue fixing method using the soft tissue fixing anchor of an embodiment of the present invention described above includes: fixing one end portion of the suture to the anchor member; inserting the anchor member to the bone cavity interior; implanting the artificial joint into the bone cavity interior while the anchor member is inserted to the bone cavity interior and the other end portion of the suture is placed at a bone cavity exterior; and suturing the other end portion of the suture to the soft tissue.

The implanting may include injecting the bone cement while the anchor member is inserted to the bone cavity interior and the other end portion of the suture is placed outside; and implanting the artificial joint into the bone cavity interior to which the bone cement is injected.

The suturing may be performed after the bone cement is hardened.

Advantageous Effects

As described above, the soft tissue fixing anchor and the soft tissue fixing method using the same according to the embodiments of the present invention may have the following effects.

According to the embodiments of the present invention, as the soft tissue fixing anchor used in a procedure of implanting an artificial joint into a bone cavity by cutting an end portion of a bone and removing a bone cavity tissue of the remaining bone, since there is provided a technical configuration including an anchor member inserted to the bone cavity interior and a suture connecting the anchor member to the soft tissue, one end portion of the suture is fixed to the anchor member before the anchor member is inserted to the bone cavity interior, the other end portion of the suture is exposed to a bone cavity exterior of the bone while the anchor member is inserted, and the other end of the suture exposed may be sutured to the soft tissue when the artificial joint is implanted into the bone cavity interior. Therefore, as the suture is first fixed by the anchor member and second fixed by the artificial joint, it is possible to prevent the suture from being released or removed from the anchor member. In particular, unlike the related art, it is possible to prevent bone loss without drilling a hole for fixing the suture to the bone and obtain a good result after the procedure even in a patient with weakened bone due to aging.

Further, according to the embodiments of the present invention, since there is provided a technical configuration in which the anchor member includes a body part and a fixing part, it is possible to prevent the suture from being removed between the bone cavity inner wall of the bone and the artificial joint through the plate-shaped body part and firmly fix one end portion of the suture by the fixing part.

Further, according to the embodiments of the present invention, since there is provided a technical configuration in which the body part of the anchor member is made of a resin material, an operator can easily cut the body part of the anchor member with scissors, etc. to fit the size of the bone cavity interior, so that the body part of the anchor member can be used universally regardless of the thickness of the bone, such as being used in the forearm with a small bone size as well as the femur with a large bone size.

DESCRIPTION OF DRAWINGS

FIG. 1 is a diagram schematically illustrating a state where a soft tissue is fixed to a bone by an existing soft tissue fixing anchor.

FIG. 2 is a diagram schematically illustrating a soft tissue fixing anchor according to an embodiment of the present invention.

FIG. 3 is a diagram schematically illustrating a state where a soft tissue is fixed to a bone by the soft tissue fixing anchor of FIG. 2.

FIG. 4 is a flowchart schematically illustrating a soft tissue fixing method according to another embodiment of the present invention.

MODES OF THE INVENTION

Hereinafter, embodiments of the present invention will be described in detail with reference to the accompanying drawings so as to be easily implemented by those skilled in the art to which the present invention pertains. However, the present invention may be embodied in many different forms and is not limited to embodiments described herein.

FIG. 2 is a diagram schematically illustrating a soft tissue fixing anchor according to an embodiment of the present invention and FIG. 3 is a diagram schematically illustrating a state where a soft tissue is fixed to a bone by the soft tissue fixing anchor of FIG. 2.

As illustrated in FIGS. 2 and 3, a soft tissue fixing anchor 100 according to an embodiment of the present invention includes an anchor member 110 and a suture 120, as a soft tissue fixing anchor used when an artificial joint A10 (FIG. 3) is implanted into a bone cavity interior G10 thereof by cutting an end portion of a bone H1 and removing a bone cavity tissue of the remaining bone H1. Hereinafter, respective components will be described in detail with reference to FIGS. 2 to 3.

The anchor member 110 is a component for fixing the suture 120 to the bone cavity interior G10. Such an anchor member 110 may be inserted to the bone cavity interior G10 as illustrated in FIGS. 2 and 3. Accordingly, when the artificial member A10 is implanted into the bone cavity interior G10, the anchor member 110 may be prevented from moving in the bone cavity interior G10 by the artificial joint A10.

On the other hand, in order to fix the artificial joint to the bone cavity interior, there are a non-cement type artificial joint implantation technique (although not illustrated, in this case, an outer wall of the artificial joint is fixed to the bone cavity inner wall by friction) of directly implanting and fixing the artificial joint into the bone cavity interior without a bone cement and a cement type artificial joint implantation technique (see FIG. 3) of first injecting the bone cement to the bone cavity interior to implant and fix the artificial joint. For example, when the anchor member 110 is applied to the non-cement type implantation technique, although not illustrated, the anchor member may serve to fix the suture. As another example, when being applied to the cement type implantation technique, as illustrated in FIGS. 2 and 3, the anchor member 110 may serve to fix the suture 120 and prevent the injected bone cement 130 from being permeated into a porous bone cavity tissue H12 below.

Particularly, when being applied to the cement type implantation technique, as illustrated in FIGS. 2 and 3, the anchor member 110 may be inserted to the bone cavity interior G10 and fixed to the bone cavity interior G10 by the bone cement 130 injected to the bone cavity interior G10. Accordingly, the suture 120 to be described below may be first fixed by the anchor member 110 and second fixed by the bone cement 130.

For example, as illustrated in FIGS. 2 and 3, the anchor member 110 may include a body part 111 and a fixing part 112. The body part 111 may have a plate shape, and when being applied to the cement type implantation technique, the body part 111 may block the bottom surface of the bone cavity interior G10 to prevent the bone cement 130 from moving to the porous bone cavity tissue H12 below. The fixing part 112 is provided in the body part 111 and may fix one end portion of the suture 120.

Further, the body part 111 may have a plate shape and may be made of a resin material. Accordingly, the operator may easily cut the body part 111 of the anchor member 110 with scissors, etc. to fit the size of the bone cavity interior G10, so that the body part 111 may be used universally regardless of the thickness of the bone, such as being used in the forearm with a small bone size as well as the femur with a large bone size. For reference, the bone H1 illustrated in FIGS. 2 and 3 shows the humerus having a middle size of the femur and the forearm.

Furthermore, the fixing part 112 may include a fixing protrusion 112a and a through hole 112b, as illustrated in FIGS. 2 and 3. The fixing protrusion 112a may protrude from an upper end of the body part 111 and the suture 120 may be fixed to the fixing protrusion 112a though the through hole 112b. Accordingly, when being applied to the cement type implantation technique, the suture 120 is fixed to the fixing protrusion 112a though the through hole 112b by drilling a hole in the fixing protrusion 112a of the fixing part 112 without drilling a hole in the body part 111 requiring the sealing of the bone cement 130, thereby maintaining a sealing effect of the body part 111 of the anchor member 110 even while fixing the suture 120.

The suture 120 is a component for connecting a soft tissue R1 and the anchor member 110. As illustrated in FIGS. 2 and 3, one end portion of the suture 120 may be fixed to the anchor member 110 and the other end portion of the suture 120 may be exposed to a bone cavity exterior to be sutured to the soft tissue R1.

In particular, one end portion of the suture 120 may be fixed to the anchor member 110 before the anchor member 110 is inserted to the bone cavity interior G10, and the other end portion of the suture 120 may be sutured to the soft tissue R1 while the anchor member 110 is inserted to the bone cavity interior G10. On the other hand, when being applied to the cement type implantation technique, the other end portion of the suture 120 may be sutured to the soft tissue R1 after the bone cement 130 injected into the bone cavity interior G10 is hardened.

Accordingly, the suture 120 may be first fixed by the anchor member 110, and second fixed between the bone cavity inner wall of the bone H1 and the artificial joint A10, and furthermore, when being applied to the cement type implantation technique, the suture 120 may be third fixed by the bone cement 130. Ultimately, the suture 120 is firmly fixed through multiple stages to be prevented from being released or removed from the anchor member 110.

Hereinafter, a soft tissue fixing member according to another embodiment of the present invention will be described with reference to FIGS. 2 to 4.

FIG. 4 is a flowchart schematically illustrating a soft tissue fixing method according to another embodiment of the present invention.

In the soft tissue fixing method according to another embodiment of the present invention, as illustrated in FIG. 4, first, one end portion of the suture 120 is fixed to the anchor member 110 (S110). Then, the anchor member 110 is inserted to the bone cavity interior G10 (S120).

Thereafter, while the anchor member 110 is inserted to the bone cavity interior G10 and the other end portion of the suture 120 is placed in the bone cavity exterior, the artificial joint A10 is implanted into the bone cavity interior G10 (S130). Then, the other end portion of the suture 120 is sutured to the soft tissue R1 (S140). At this time, the suturing may be performed while the soft tissue R1 is sufficiently pulled.

Further, when being applied to the cement type implantation technique, the above-described implanting process (S130) may include injecting the bone cement 130 while the anchor member 110 is inserted to the bone cavity interior G10 and the other end portion of the suture 120 is placed in the bone cavity exterior and implanting the artificial joint A10 into the bone cavity interior G10 to which the bone cement 130 is injected.

Further, the above-described suturing process (S140) may be performed after the bone cement 130 is hardened.

While the preferred embodiments of the present invention have been described in detail, the scope of the present invention is not limited thereto and also covers various modifications and changes of those skilled in the art using a basic concept of the present invention which is defined in appended claims.

[Explanation of Reference Numerals and Symbols]

| | |
|---|---|
| 100: Soft tissue fixing anchor | 110: Anchor member |
| 111: Body part | 112: Fixing part |
| 112a: Fixing protrusion | 112b: Through hole |
| 120: Suture | 130: Bone cement |
| H1: Bone (humerus) | S1: Bone (scapula) |
| R1: Soft tissue (rotator cuff) | G10: Bone cavity interior |
| A10: Artificial joint | |

The invention claimed is:

1. A soft tissue fixing method, comprising:
providing a soft tissue fixing anchor comprising:
an anchor member which is configured to be inserted to a bone cavity interior and prevented from moving in the bone cavity interior by an artificial joint when the artificial joint is implanted; and
a suture of which one end portion is configured to be fixed to the anchor member and the other end portion is configured to be exposed to a bone cavity exterior of the bone so as to be sutured to soft tissue;
fixing the one end portion of the suture to the anchor member;
inserting the anchor member to the bone cavity interior;
implanting the artificial joint into the bone cavity interior while the anchor member is inserted to the bone cavity interior and the other end portion of the suture is placed at the bone cavity exterior; and
suturing the other end portion of the suture to the soft tissue.

2. A soft tissue fixing method, comprising:
providing a soft tissue fixing anchor comprising:
an anchor member which is configured to be inserted to a bone cavity interior and prevented from moving in the bone cavity interior by an artificial joint when the artificial joint is implanted; and
a suture of which one end portion is configured to be fixed to the anchor member and the other end portion is configured to be exposed to a bone cavity exterior of the bone so as to be sutured to soft tissue;
wherein the anchor member comprises a plate-shaped body part and a fixing part provided in the body part to affix one end portion of the suture;
fixing the one end portion of the suture to the anchor member;
inserting the anchor member to the bone cavity interior;
implanting the artificial joint into the bone cavity interior while the anchor member is inserted to the bone cavity interior and the other end portion of the suture is placed at the bone cavity exterior; and
suturing the other end portion of the suture to the soft tissue.

* * * * *